United States Patent
Gittleman

[11] Patent Number: 5,564,928
[45] Date of Patent: Oct. 15, 1996

[54] RETRIEVABLE CEMENTED PROSTHODONTIC APPARATUS

[76] Inventor: Neal B. Gittleman, 15 Greenway Plz. #1-D, Houston, Tex. 77046

[21] Appl. No.: 374,933

[22] Filed: Jan. 18, 1995

[51] Int. Cl.⁶ .......................... A61C 13/12; A61C 13/225
[52] U.S. Cl. .............................. 433/180; 433/148
[58] Field of Search .................................. 433/172, 173, 433/174, 180, 181

[56] References Cited

U.S. PATENT DOCUMENTS

| | | | |
|---|---|---|---|
| 4,416,629 | 11/1983 | Mozsary et al. | 433/174 |
| 5,073,111 | 12/1991 | Daftary | 433/173 |
| 5,106,299 | 4/1992 | Ghalili | 433/172 |

Primary Examiner—Robert P. Swiatek
Assistant Examiner—Yvonne R. Abbott
Attorney, Agent, or Firm—Ezra L. Schacht

[57] ABSTRACT

A method and apparatus for setting and removing a cemented, retrievable prosthodontic appliance using a levering instrument applied to the gap between two parallel surfaces, the first surface being a flat-topped ledge of a window on the lingual aspect of a dental prosthesis and the second surface being at least one opposed step or ledge on an artificial implant abutment. This invention combines the evenly stressed strength of a permanently cemented prosthesis with a damage free method of prosthesis removal without undue forces on the underlying implant.

2 Claims, 3 Drawing Sheets

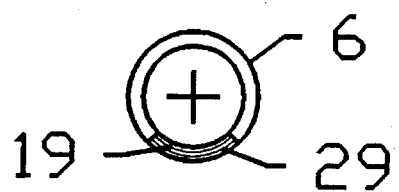
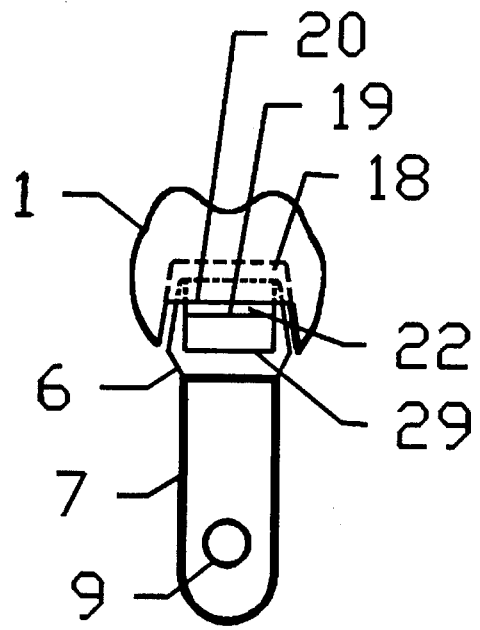
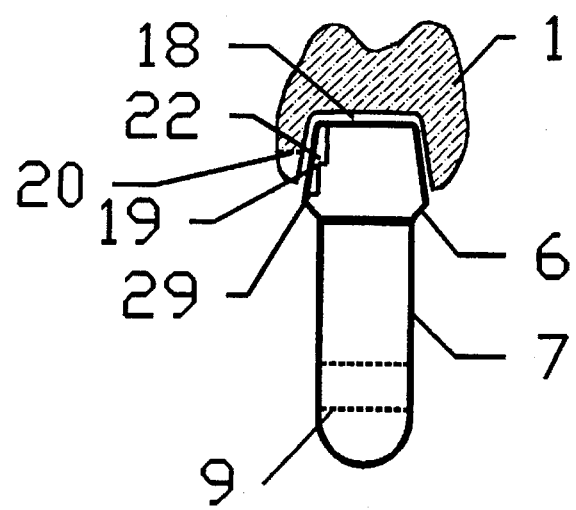

RETRIEVABLE CEMENTED PROSTHODONTIC APPARATUS

BACKGROUND OF THE INVENTION

In Disclosure Document No. 367510, submitted to the PTO on 27 Dec. 27, 1994, there appears much of the material in this specification.

Present dental practices tend toward the replacement of lost teeth with cylindrical or plate metal alloy implants embedded in the bone of the mandible or maxilla to support the artificial tooth restoration. If extensive replacement of several teeth is needed, several implants, alone or in conjunction with existing teeth prepared as abutments, are used to anchor the replacement prosthetic teeth. As the number and complexity of support abutments are increased, the difficulty in aligning and fastening the prosthetic restoration increases. The use of several mechanically connected parts at each post or plate implant site, adds to the possibility of misalignment or biomechanical failure. This invention describes a method and apparatus to provide a simpler mechanism and more direct technique for securing a permanently cemented, yet retrievable prosthodontic appliance while still offering a durable mechanical support. The last two decades have led to a revolution in implant prosthodontics. Titanium alloy implant cylinders or plates are intimately installed in holes or slots drilled in the underlying bone. It is the practice to allow several months to pass while the underlying bone bonds to the surface of the implant. For this reason, implants are provided with at least one threaded hole on the crestal surface or edge. These holes are temporarily capped with a healing screw to prevent the downgrowth of soft tissue and bone into the internal threads. The soft tissue is sutured over the implant until the intimate metal-bone bond is effected.

At the next surgical encounter, the soft tissue is resected and the healing screw is replaced with a metal alloy perimucosal extension of selectable height and emergence profile and the soft tissue is sutured around the base of this extension. This extension is usually bolted in place and prevented from rotating by means of locating pins and holes or internal and external matching hexagonal (or other regular polygon shaped) projections. These perimucosal extensions form the support for artificial abutments used to support the final prosthetic restoration. The final prosthodontic restoration requires a close mechanical mating between the abutments and the matching internal aspect or underside of the prosthesis. These closely matched parts often consist of telescoped, tapered cylindrical surfaces requiring a tight, non-binding, "passive" fit. This places inordinate requirements on the precision and technical skills of the dentist and the laboratory technician. Parallel alignment of the axes of each abutment to prevent binding of tapered fits cannot be easily guaranteed. The present invention, relying on a conformable, cemented boundary, circumvents these objections.

Much of the current discussion in the field of dental implantology centers around the durability and maintainability of the various methods of attaching the final restoration to the underlying abutments. Bolting with threaded fasteners through the occlusal surface of the restoration and back filling with composite materials complicate the cosmetics and the retrievability of the prosthesis. Bolting through the non cosmetic, lingual side of the prosthesis has the additional requirement for a greater thickness of metal to provide mechanical support, thus reducing room for the tongue and potentially affecting speech, and the periodontal health of the abutment.

Excessive inline or rocking pressure transmitted to an individual implant from the overlying restoration may lead to frank implant failure. Failures may occur from the loosening of a screw caused by thread walking or the backing out of a screw by micro-movements. The shifting of an abutment from repetitive stresses exceeding the elastic limits between the screw thread and the internal thread of the implanted post or plate may cause the flexure or excessive loading of a single implant. Long term changes in the underlying bone structure in response to uneven stresses may lead to the loss of an individual dental implant. For each additional mechanically attached connection, alignment errors accumulate and reduce the likelihood of a good non-binding, stress free "passive" fit.

The present invention acts to equitably distribute the loading forces with a retrievable dental cement between the matching faces of the abutments and the internal aspect of the final restoration. Each abutment is made with at least one step or shelf on the lingual face to act as a bearing surface for a removal instrument. The final prosthesis is equipped with a flat-topped window ledge on the lingual side. There is a matching shelf on the implant abutment, with enough space between the surface of the shelf and the flat top of the window for the introduction of a wedge-tipped extraction instrument. This instrument is used to apply a prying force between each abutment and the mating ledge in the underside of the final restoration. The prying instrument applies an even opposing force between the overstructure and the abutment eliminating the potential damage to both structures. Prior methods of removing cemented restorations involved hammering movements under much less control. The method and apparatus of this invention in combination with an appropriate dental cement, yields a predictable technique for securing, yet retrieving the final restoration.

A BRIEF DESCRIPTION OF THE DRAWINGS

FIG. 1 shows a cross sectional elevated view of a final restoration with various means of support.

FIGS. 2a and 2b display a cross sectional front and side view of a single implant with abutment "steps" and secondary restoration with "window".

FIGS. 2c is a top view of the abutment.

FIG. 3 details a cross sectional view of the prying instrument in use.

DETAILED DESCRIPTION OF THE DRAWINGS.

Figure 1:
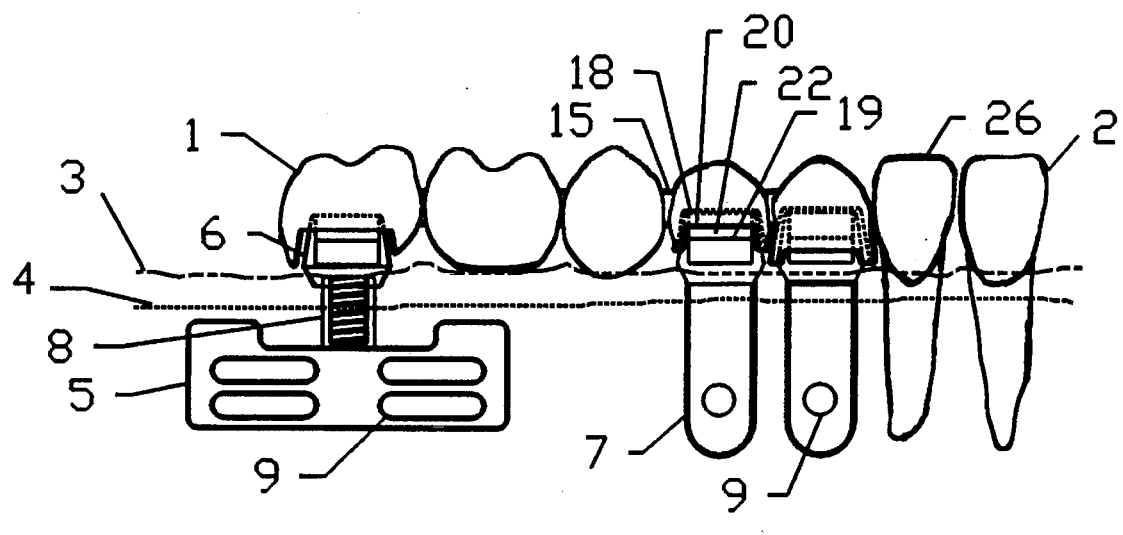

The partially edentulous lower left jaw, shown schematically in elevated view from the lingual side in FIG. 1, illustrates the combination of methods used to secure the secondary prosthesis 1. Natural tooth 2 is not modified, nor is its nearest neighbor 26. The next five dental positions are replaced with the prosthesis 1, with each artificial tooth bridged by the underlying structural member 15. The bone surface 4 is shown with it's overlying soft tissue margin 3. Typical plate implant 5 and post implant 7 are firmly set within the bone 4 with extension penetrating through the soft tissue 3. The plate extension 8 has an internal thread and coupling means to retain tapered and stepped abutment 6. Post implant 7 rises through the soft tissue margin 3 and terminates in a similar tapered and stepped abutment. This abutment has a step or shelf 19 shown extending for a distance circumferentially around the long axis of the post implant and opposing the parallel, flat-topped ledge 20 of a lingual side window in the prosthetic appliance. The gap 22 between these two parallel surfaces allows for the introduction of a prying or twisting tool to part the overlying prosthesis from the abutment underneath.

Cement applied within the bonding space 18 between the prosthesis and the abutment acts to firmly retain the prosthesis to the abutments with an even distribution of forces. This prevents any undue stresses on any one abutment.

FIG. 2a presents an elevated view of a typical single post implant 7 with a perforation 9 to allow for ingress of bone growth for additional reinforcement. Prosthesis 1 may be removed by application of opposing force between surface 20 of the prosthesis and surface 19 of the post abutment 6. Since the forces are in opposition, minimal pulling or twisting forces are transmitted to implant post 7 with less chance of loosening the implant or breaking the prosthesis. Multiple shelves 19 and 29 accommodate different elevations for the proper design of and access to the window of the prosthesis. FIG. 2c shows the plan view of the top of the abutment post with the shelves or steps 19 and 29 extending for some distance around the circumference of the post abutment 6.

Figure 3:
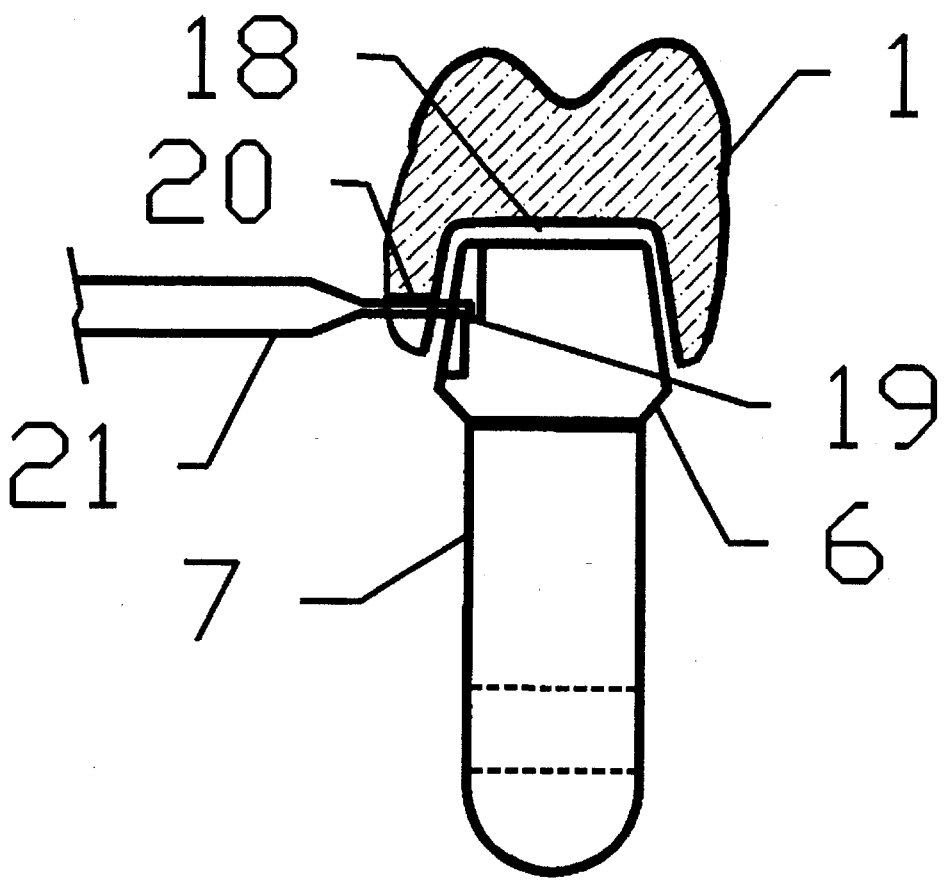

FIG. 2b shows the elevated sectional view through the post implant 7. Shelf 19 and opposing flat-topped window ledge 20 show the area of force application. FIG. 3 illustrates the use of a tool 21 to pry between shelf 19 and ledge 20 to part the cement in the bonding space 18 by the application of levered force. The proper choice of cement joining the surface of abutment 6 and the internal aspect of prosthesis 1 determines the maximum force needed for removal.

FIG. 3 gives an elevated sectional view of one member of the prosthesis 1 and a post implant 7 with its attached abutment 6. The step or shelf 19 of the abutment 6 and the opposing flat-topped ledge 20 of the window in prosthesis 1 form the gapped parallel mating surfaces against which the prying instrument is worked. The flat blade of the prying instrument applies force to the opposing surfaces 19 and 20 and shears the cement bond in the bonding space 18 to release the fixed retrievable prosthesis 1.

Whereas these drawings and descriptions shown herein for the purpose of illustrating the invention show more than one tooth being replaced, the method and apparatus described apply to a single tooth replacement site. These and other variations of the present invention may be made which fall within the scope of the appended claims even though such variations were not related above.

The accompanying drawings referred to herein are illustrative of the invention but not restrictive thereto, and, together with the description, serve to explain the principles of the invention.

What is claimed is:

1. A dental apparatus having at least one dental implant abutment, at least one abutment having at least one flat shelf; and a cementable, retrievable prosthesis, mating with said at least one abutment, said prosthesis having at least one flat window ledge in proximity to and parallel to said at least one abutment shelf, forming a gapped space of opposing surfaces for the entrance of a prying instrument to separate said prosthesis from said at least one abutment.

2. A method of removing a cemented prosthesis from at least one dental implant abutment, the at least one abutment having at least one flat shelf, the shelf mating with at least one flat window ledge of said prosthesis, said at least one flat ledge and said at least one flat shelf forming a gapped space of opposing surfaces;

the steps of the method comprising:

(a) introducing into said gapped space an instrument for prying action within said gapped space;

(b) prying wider said gapped space to separate said cement and (c) releasing said cemented prosthesis from said at least one dental implant abutment.

\* \* \* \* \*